(12) United States Patent
Petermann et al.

(10) Patent No.: US 11,142,633 B2
(45) Date of Patent: Oct. 12, 2021

(54) AQUEOUS COMPOSITION COMPRISING DISPERSED ESTERIFIED CELLULOSE ETHER

(71) Applicant: Dow Global Technologies LLC, Midland, MI (US)

(72) Inventors: Oliver Petermann, Hamburg (DE); Matthias Knarr, Nienburg/Weser (DE); Meinolf Brackhagen, Walsrode (DE)

(73) Assignee: Nutrition & Biosciences USA 1, LLC, Rochester, NY (US)

( * ) Notice: Subject to any disclaimer, the term of this patent is extended or adjusted under 35 U.S.C. 154(b) by 152 days.

(21) Appl. No.: 15/764,498

(22) PCT Filed: Sep. 29, 2016

(86) PCT No.: PCT/US2016/054271
§ 371 (c)(1),
(2) Date: Mar. 29, 2018

(87) PCT Pub. No.: WO2017/058973
PCT Pub. Date: Apr. 6, 2017

(65) Prior Publication Data
US 2018/0282526 A1     Oct. 4, 2018

Related U.S. Application Data

(60) Provisional application No. 62/236,173, filed on Oct. 2, 2015.

(51) Int. Cl.
| | | |
|---|---|---|
| C08L 1/32 | (2006.01) | |
| A23L 33/10 | (2016.01) | |
| A61K 9/48 | (2006.01) | |
| A61K 47/38 | (2006.01) | |
| A23P 10/30 | (2016.01) | |
| B29C 41/14 | (2006.01) | |
| C08B 13/00 | (2006.01) | |
| C08B 1/00 | (2006.01) | |
| B29K 1/00 | (2006.01) | |
| B29L 31/00 | (2006.01) | |

(52) U.S. Cl.
CPC ............ *C08L 1/32* (2013.01); *A23L 33/10* (2016.08); *A23P 10/30* (2016.08); *A61K 9/4816* (2013.01); *A61K 9/4833* (2013.01); *A61K 47/38* (2013.01); *B29C 41/14* (2013.01); *C08B 13/00* (2013.01); *A23V 2002/00* (2013.01); *B29K 2001/08* (2013.01); *B29L 2031/7174* (2013.01); *C08L 2201/06* (2013.01); *C08L 2203/02* (2013.01); *C08L 2205/025* (2013.01)

(58) Field of Classification Search
None
See application file for complete search history.

(56) References Cited

U.S. PATENT DOCUMENTS

| | | | | |
|---|---|---|---|---|
| 3,499,040 | A * | 3/1970 | Stanin | .................... C08G 63/66 |
| | | | | 568/612 |
| 4,226,981 | A | 10/1980 | Onda et al. | |
| 4,365,060 | A | 12/1982 | Onda et al. | |
| 5,539,021 | A | 7/1996 | Pate et al. | |
| 7,763,676 | B2 | 7/2010 | Moncla et al. | |
| 2007/0087939 | A1* | 4/2007 | Cade | .................... A61K 9/4816 |
| | | | | 504/359 |
| 2013/0102691 | A1* | 4/2013 | Miller | .................... A61K 9/146 |
| | | | | 514/781 |
| 2013/0295188 | A1* | 11/2013 | Cade | .................... A61K 9/4816 |
| | | | | 424/494 |
| 2014/0370091 | A1* | 12/2014 | Kikuchi | ............... A61K 31/525 |
| | | | | 424/480 |

FOREIGN PATENT DOCUMENTS

| | | | | |
|---|---|---|---|---|
| EP | 0219426 | | 4/1987 | |
| ES | 2728850 T3 * | 10/2019 | ........... A61K 9/4816 |
| WO | 2005115330 | | 12/2005 | |
| WO | 2008119943 | | 10/2008 | |
| WO | 2013148154 A1 | 10/2013 | |

(Continued)

OTHER PUBLICATIONS

ES2728850T3 translation, accessed from: "https://patents.google.com/patent/ES2728850T3/en?q=degree+neutralization+hpmcas&oq=degree+neutralization+hpmcas", accessed on Mar. 27, 2020, pp. 1-19 (Year: 2020).*

(Continued)

*Primary Examiner* — Michael G. Hartley
*Assistant Examiner* — Lance W Rider (57) ABSTRACT

An aqueous composition which is useful for producing coatings and capsule shells comprises a) dispersed particles of an esterified cellulose ether comprising (i) groups of the formula —C(O)—R—COOA or (ii) a combination of aliphatic monovalent acyl groups and groups of the formula —C(O)—R—COOA, wherein R is a divalent hydrocarbon group and A is hydrogen or a cation, and the total degree of ester substitution is more than 0.70, and b) an esterified cellulose ether comprising aliphatic monovalent acyl groups and groups of the formula —C(O)—R—COOH, R being a divalent hydrocarbon group, wherein I) the degree of neutralization of the groups —C(O)—R—COOH is not more than 0.4, II) the total degree of ester substitution is from 0.03 to 0.70, and III) the esterified cellulose ether b) has a solubility in water of at least 2.0 weight percent at 2° C.

21 Claims, 3 Drawing Sheets

(56) References Cited

FOREIGN PATENT DOCUMENTS

| WO | WO-2013154607 A1 | * | 10/2013 |
|----|------------------|---|---------|
| WO | 2013164121 | | 11/2013 |
| WO | 2013164122 A1 | | 11/2013 |
| WO | 2014137777 A1 | | 9/2014 |
| WO | 2015156922 A1 | | 10/2015 |
| WO | 2016148977 A1 | | 9/2016 |

OTHER PUBLICATIONS

Nichetti, D., et al. "Viscosity model for polydisperse polymer melts" J. Rheology, pp. 951-969 (Year: 1998).*

* cited by examiner

AQUEOUS COMPOSITION COMPRISING DISPERSED ESTERIFIED CELLULOSE ETHER

FIELD

This invention concerns aqueous compositions comprising dispersed esterified cellulose ethers and the use of the aqueous compositions for coating dosage forms and producing capsule shells.

INTRODUCTION

Esters of cellulose ethers, their uses and processes for preparing them are generally known in the art. Known methods of producing cellulose ether-esters include the reaction of a cellulose ether with an aliphatic monocarboxylic acid anhydride or a dicarboxylic acid anhydride or a combination thereof, for example as described in U.S. Pat. Nos. 4,226,981 and 4,365,060.

Various known esterified cellulose ethers are useful as enteric polymers for pharmaceutical dosage forms, such as methylcellulose phthalate (MCP), hydroxypropyl methylcellulose phthalate (HPMCP), methylcellulose succinate (MCS), or hydroxypropyl methylcellulose acetate succinate (HPMCAS). The esterified cellulose ethers are used for coating dosage forms, such as tablets, microparticulates or capsules. Enteric polymers protect the drug from inactivation or degradation in the acidic environment or prevent irritation of the stomach by the drug, but are dissolved in the intestinal canals to release the drug contained therein. U.S. Pat. No. 4,365,060 discloses enterosoluble capsules which are said to have excellent enterosolubility behavior.

International Patent Application WO 2013/164122 discusses the challenges when producing shells and capsules of controlled release properties, specifically enterosolubility behavior. Typically first hard or soft capsules are formed and then the pre-manufactured capsules are surface-treated with one or more layers of a substance or composition that is known to impart enteric properties. However, this multi-step process is complex. To overcome the drawbacks of multiple processing steps, another technique used to impart controlled release properties to hard or soft capsule shells involves the direct use of controlled release polymers (for example acid-insoluble polymers). However, this requires the use of a large amount of enteric polymers. At the required large amounts enteric polymers are poorly or completely water insoluble, therefore rendering the process impracticable to be used on a commercial scale. WO 2013/164122 discloses that attempts to overcome the deficiencies discussed above include (i) using low, water-soluble amounts of acid-insoluble polymers in combination with major amounts of conventional film forming polymers; (ii) salifying the water-insoluble polymers to obtain water-soluble derivatives; (iii) using solvent-based dipping solutions instead of water-based ones; and (iv) using alternative techniques which do not require polymer solubilization, such as injection moulding.

Specifically, International Patent Application WO 2008/119943 discloses a capsule comprising (a) a film-forming, water-soluble polymer, such as hydroxypropyl methyl cellulose (HPMC), (b) an acid-insoluble polymer, such as an alginate, a (meth)acrylic acid copolymer, or a cellulose acetate ester such as phthalate, butyrate, hydroxypropyl methyl cellulose phthalate; and salts thereof, (c) a gelatinizing agent, (d) an auxiliary for gelation, and (e) a plasticizer. Unfortunately, the use of HPMC as water-soluble film-forming polymer may impact the enteric performance of the capsule. HPMC is not an enteric polymer, i.e., it is soluble in the acidic environment of the stomach.

International Patent Application WO 2013/164122 tries to overcome the above-mentioned disadvantages by an aqueous composition for the manufacture of capsule shells comprising 5-50 wt. % of a wide range of functional polymers. In the majority of the examples the capsules are produced from an Aquacoat CPD 30 dispersion, which is a 30 wt % aqueous dispersion comprising 23 wt. % non-salified cellulose acetate phthalate (CAP) and 7 wt. % Poloxamer, optionally blended with a minor amount of a HPMCAS slurry. Often uniform films can be obtained. A HPMCAS dispersion comprising 14% solids is also disclosed. 20% Triethyl citrate is used as a film forming aid. However, when pins are heated to 50° C. and dipped into the dispersion, the HPMCAS polymer aggregates but the film rapidly collapses and flows down.

In view of the deficiencies of the prior art it would be desirable to find new aqueous compositions of esterified cellulose ethers which are useful for coating dosage forms or for producing capsule shells without jeopardizing the enteric properties of the esterified cellulose ethers. It would be particularly desirable to find new compositions of esterified cellulose ethers of which the viscosities can be adjusted to the particular end-use of the composition without jeopardizing the enteric properties of the esterified cellulose ethers.

SUMMARY

One aspect of the present invention is an aqueous composition which comprises a) dispersed particles of an esterified cellulose ether comprising (i) groups of the formula —C(O)—R—COOA or (ii) a combination of aliphatic monovalent acyl groups and groups of the formula —C(O)—R—COOA, wherein R is a divalent hydrocarbon group and A is hydrogen or a cation, and the total degree of ester substitution is more than 0.70, and b) an esterified cellulose ether comprising aliphatic monovalent acyl groups and groups of the formula —C(O)—R—COOH, R being a divalent hydrocarbon group, wherein I) the degree of neutralization of the groups —C(O)—R—COOH is not more than 0.4, II) the total degree of ester substitution is from 0.03 to 0.70, and III) the esterified cellulose ether b) has a solubility in water of at least 2.0 weight percent at 2° C.

Another aspect of the present invention is a dosage form which is coated with a coating prepared from the above-mentioned aqueous composition.

Yet another aspect of the present invention is a capsule shell which is made from the above-mentioned aqueous composition.

Yet another aspect of the present invention is a capsule which comprises an above-mentioned capsule shell and further comprises a drug or a nutritional or food supplement or a combination thereof.

Yet another aspect of the present invention is a process for producing capsule shells which comprises the steps of providing the above-mentioned aqueous composition, preheating molding pins to a temperature higher than the aqueous composition, dipping the pre-heated molding pins into the aqueous composition, forming a film on said molding pins by withdrawing said pins from said aqueous composition, and drying the film on the molding pins.

DESCRIPTION OF EMBODIMENTS

Various known esterified cellulose ethers dispersed in aqueous compositions, such as hydroxypropyl methylcellulose acetate succinate (HPMCAS) particles become tacky and tend to agglomeration in aqueous dispersions at elevated temperatures. Finally the HPMCAS particles start to agglomerate and the viscosity of the aqueous HPMCAS dispersion starts to significantly increase. The temperature at which the HPMCAS particles start to agglomerate in the aqueous dispersion is designated hereafter as "phase transition temperature" of the dispersion.

A high viscosity of an aqueous dispersion comprising HPMCAS particles is desired when the aqueous dispersion is used for forming capsule shells on dipping pins or in some coating processes. The high viscosity of the aqueous dispersion at a selected processing temperature improves adherence of the aqueous dispersion to the dipping pins and also to other substrate to be coated such as tablets. In the capsule manufacturing process and in some coating processes the aqueous dispersion is generally subjected to only low shear, e.g., to gentle stirring of the aqueous dispersion for homogenization purposes.

On the other hand, a high viscosity is often undesirable when the HPMCAS particles are subjected to high shear, e.g. when HPMCAS particles are to be mixed with other materials during preparation of HPMCAS dispersions, when the esterified cellulose ether particles are subjected to grinding in the presence of water to produce the aqueous dispersion or when the aqueous dispersion is used for spraying purposes.

The present invention as described in more details below enables a viscosity increase and a tailor-made adjustment of the viscosity of the aqueous dispersion at low shear, while still maintaining a reasonably low viscosity, and hence a reasonably good handling of the aqueous dispersion at higher shear. "Low shear" as used herein means a shear rate of not more than about 200 $sec^{-1}$. In contrast to known thickening agents, the tailor-made viscosity increase is achieved by incorporating a new water-soluble esterified cellulose ether in the aqueous composition. Such water-soluble esterified cellulose ethers are described in copending International Patent Application No. PCT/US16/021330, filed on 8 Mar. 2016, which claims the priority of U.S. Provisional Application No. 62/133,514, filed 16 Mar. 2015, and International Patent Application No. PCT/US16/021326, filed on 8 Mar. 2016, which claims the priority of U.S. Provisional Application No. 62/133,518, filed on 16 Mar. 2015, all filed by the Applicants of the present patent application. Because water-soluble esterified cellulose ethers are used as a thickener which have a similar chemical structure as the dispersed particles of an esterified cellulose ether in the aqueous composition, the incorporation of this thickener into the aqueous composition does not reduce or even jeopardize the desired properties provided by the dispersed particles of the esterified cellulose ether, such as enteric properties.

The esterified cellulose ethers a) and b) comprised in the aqueous composition of the present invention have a cellulose backbone having β-1,4 glycosidically bound D-glucopyranose repeating units, designated as anhydroglucose units in the context of this invention. The esterified cellulose ethers preferably are esterified alkyl celluloses, hydroxyalkyl celluloses or hydroxyalkyl alkylcelluloses. This means that in the esterified cellulose ethers comprised in the composition of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ethers. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ethers are esterified hydroxyalkyl methylcelluloses, such as esterified hydroxypropyl methylcelluloses.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylating agent, e.g. a methylating agent, and/or a hydroxyalkylating agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxyl units are covalently bound to each other by ether bonding. Within this definition it is not important whether the terminal hydroxyl group of a hydroxyalkoxyl substituent is further alkylated or not; both alkylated and non-alkylated hydroxyalkoxyl substituents are included for the determination of MS(hydroxyalkoxyl). The esterified cellulose ethers a) and b) generally have a molar substitution of hydroxyalkoxyl groups of at least 0.05, preferably at least 0.08, more preferably at least 0.12, and most preferably at least 0.15. The degree of molar substitution is generally not more than 1.00, preferably not more than 0.90, more preferably not more than 0.70, and most preferably not more than 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers a) and b) preferably have a DS(alkoxyl) of at least 1.0, more preferably at least 1.1, even more preferably at least 1.2, most preferably at least 1.4, and particularly at least 1.6. The DS(alkoxyl) is preferably not more than 2.5, more preferably not more than 2.4, even more preferably not more than 2.2, and most not more than 2.05.

Most preferably the esterified cellulose ethers a) and b) are esterified hydroxypropyl methylcelluloses having a DS(methoxyl) within the ranges indicated above for DS(alkoxyl) and an MS(hydroxypropoxyl) within the ranges indicated above for MS(hydroxyalkoxyl).

The esterified cellulose ether which is present as dispersed particles a) in the aqueous composition of the present invention has (i) groups of the formula —C(O)—R—COOA or (ii) a combination of aliphatic monovalent acyl groups and groups of the formula —C(O)—R—COOA, wherein R is a divalent hydrocarbon group and A is hydrogen or a cation. The cation preferably is an ammonium cation, such as $NH_4^+$ or an alkali metal ion, such as the sodium or potassium ion, more preferably the sodium ion. Most preferably, A is hydrogen.

The esterified cellulose ether b) which is also present in the aqueous composition of the present invention has aliphatic monovalent acyl groups and groups of the formula —C(O)—R—COOH.

The aliphatic monovalent acyl groups which are present in the esterified cellulose ether b) and optionally in the esterified cellulose ether a) are preferably acetyl, propionyl, or butyryl, such as n-butyryl or i-butyryl. Preferred groups of the formulas —C(O)—R—COOA and —C(O)—R—COOH are —C(O)—CH$_2$—CH$_2$—COOA and —C(O)—CH$_2$—CH$_2$—COOH.

Specific examples of esterified cellulose ethers a) and b) are hydroxypropyl methylcellulose acetate succinate (HPMCAS), hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); or methyl cellulose acetate succinate (MCAS). Hydroxypropyl methylcellulose acetate succinates (HPMCAS) are the most preferred esterified cellulose ethers a) and b).

In the esterified cellulose ether b) the degree of neutralization of the groups —C(O)—R—COOH is not more than 0.4, preferably not more than 0.3, more preferably not more than 0.2, most preferably not more than 0.1, and particularly not more than 0.05 or even not more than 0.01. The degree of neutralization can even be essentially zero or only slightly above it, e.g. up to $10^{-3}$ or even only up to $10^{-4}$. The term "degree of neutralization" as used herein defines the ratio of deprotonated carboxylic groups over the sum of deprotonated and protonated carboxylic groups, i.e., $$\text{Degree of neutralization} = [\text{—C(O)—R—COO}^-]/[\text{—C(O)—R—COO}^- + \text{—C(O)—R—COOH}].$$

If the groups —C(O)—R—COOH are partially neutralized, the cation preferably is an ammonium cation, such as $NH_4^+$ or an alkali metal ion, such as the sodium or potassium ion, more preferably the sodium ion.

In the esterified cellulose ether a) the degree of neutralization of the groups —C(O)—R—COOH can be more than 0.4, but preferably it is within the ranges indicated above for the degree of neutralization of the groups —C(O)—R—COOH in the esterified cellulose ether b).

The esterified cellulose ether which is present as dispersed particles a) in the aqueous composition of the present invention is distinct from the esterified cellulose ether b) by its total degree of ester substitution. In the dispersed particles of the esterified cellulose ether a) the total degree of ester substitution, i.e. the sum of i) the degree of substitution of aliphatic monovalent acyl groups and ii) the degree of substitution of groups of formula —C(O)—R—COOA is more than 0.70, preferably at least 0.75, and more preferably at least 0.80. The mentioned sum is generally no more than 2.0, preferably no more than 1.4, more preferably no more than 1.15, most preferably no more than 1.10 and particularly no more than 1.00.

In the dispersed particles of the esterified cellulose ether a) the degree of substitution of aliphatic monovalent acyl groups, such as acetyl, propionyl, or butyryl groups, is generally not more than 1.75, preferably not more than 1.50, more preferably not more than 1.25, and most preferably not more than 1.00, or even not more than 0.65. The degree of substitution of aliphatic monovalent acyl groups can be zero, but preferably it is at least 0.05, more preferably at least 0.10, and most preferably at least 0.20. In the dispersed particles of the esterified cellulose ether a) the degree of substitution of groups of formula —C(O)—R—COOA, such as succinoyl, is at least 0.05, preferably at least 0.10. The degree of substitution of groups of formula —C(O)—R—COOA generally is up to 1.6, preferably up to 1.30, more preferably up to 1.00, and most preferably up to 0.70 or even up to 0.60. The degree of substitution of i) aliphatic monovalent acyl groups and ii) groups of formula —C(O)—R—COOA are chosen that their sum is more than 0.70, as described above.

The esterified cellulose ether b) in the aqueous composition of the present invention has aliphatic monovalent acyl groups and groups of the formula —C(O)—R—COOH, such that the total degree of ester substitution is from 0.03 to 0.70. The sum of i) the degree of substitution of aliphatic monovalent acyl groups and ii) the degree of substitution of groups of formula —C(O)—R—COOH, of which the degree of neutralization is not more than 0.4, is an essential feature of the esterified cellulose ether b). The total degree of ester substitution is at least 0.03, generally at least 0.07, preferably at least 0.10, more preferably at least 0.15, most preferably at least 0.20, and particularly at least 0.25. The total degree of ester substitution in the esterified cellulose ether b) is not more than 0.70, generally not more than 0.67, preferably up to 0.65, more preferably up to 0.60, and most preferably up to 0.55 or up to 0.50. In one aspect of the present invention esterified cellulose ethers b) having a total degree of ester substitution of from 0.10 to 0.65 and particularly from 0.20 to 0.60 are preferred. In another aspect of the present invention esterified cellulose ethers b) having a total degree of ester substitution of from 0.20 to 0.50 and particularly from 0.25 to 0.44 are preferred.

The esterified cellulose ethers b) generally have a degree of substitution of aliphatic monovalent acyl groups, such as acetyl, propionyl, or butyryl groups, of at least 0.03 or 0.05, preferably at least 0.10, more preferably at least 0.15, most preferably at least 0.20, and particularly at least 0.25 or at least 0.30. The esterified cellulose ethers generally have a degree of substitution of aliphatic monovalent acyl groups of up to 0.69, preferably up to 0.60, more preferably up to 0.55, most preferably up to 0.50, and particularly up to 0.45 or even only up to 0.40. The esterified cellulose ethers b) generally have a degree of substitution of groups of formula —C(O)—R—COOH, such as succinoyl, of at least 0.01, preferably at least 0.02, more preferably at least 0.05, and most preferably at least 0.10. The esterified cellulose ethers generally have a degree of substitution of groups of formula —C(O)—R—COOH of up to 0.65, preferably up to 0.60, more preferably up to 0.55, and most preferably up to 0.50 or up to 0.45. As indicated above, the degree of neutralization of the groups —C(O)—R—COOH is not more than 0.4.

Moreover, in the esterified cellulose ether b) the sum of i) the degree of substitution of aliphatic monovalent acyl groups and ii) the degree of substitution of groups of formula —C(O)—R—COOH and iii) the degree of substitution of alkoxyl groups, DS(alkoxyl), generally is not more than 2.60, preferably not more than 2.55, more preferably not more than 2.50, and most preferably not more than 2.45. The esterified cellulose ether b) generally has a sum of degrees of substitution of i) aliphatic monovalent acyl groups and ii) groups of formula —C(O)—R—COOH and iii) of alkoxyl groups of at least 1.7, preferably at least 1.9, and most preferably at least 2.1.

The content of the acetate and succinate ester groups is determined according to "Hypromellose Acetate Succinate", United States Pharmacopeia and National Formulary, NF 29, pp. 1548-1550. Reported values are corrected for volatiles (determined as described in section "loss on drying" in the above HPMCAS monograph). The method may be used in analogue manner to determine the content of propionyl, butyryl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) -$$
$$\left(\% \text{ HPO} * \frac{M(OCH_2CH(OH)CH_3) - M(OH)}{M(OCH_2CH(OH)CH_3)}\right) -$$
$$\left(\% \text{ Acetyl} * \frac{M(COCH_3) - M(H)}{M(COCH_3)}\right) -$$
$$\left(\% \text{ Succinoyl} * \frac{M(COC_2H_4COOH) - M(H)}{M(COC_2H_4COOH)}\right)$$

$$DS(Me) = \frac{\frac{\% \text{ MeO}}{M(OCH_3)}}{\frac{\% \text{ cellulose backbone}}{M(AGU)}}$$

-continued $$MS(HP) = \frac{\frac{\% \text{ HPO}}{M(HPO)}}{\frac{\% \text{ cellulose backbone}}{M(AGU)}}$$

$$DS(Acetyl) = \frac{\frac{\% \text{ Acetyl}}{M(Acetyl)}}{\frac{\% \text{ cellulose backbone}}{M(AGU)}}$$

$$DS(Succinoyl) = \frac{\frac{\% \text{ Succinoyl}}{M(Succinoyl)}}{\frac{\% \text{ cellulose backbone}}{M(AGU)}}$$

$M(MeO) = M(OCH_3) = 31.03 \ Da$ $M(HPO) = M(OCH_2CH(OH)CH_3) = 75.09 \ Da$ $M(Acetyl) = M(COCH_3) = 43.04 \ Da$ $M(Succinoyl) = M(COC_2H_4COOH) = 101.08 \ Da$ $M(AGU) = 162.14 \ Da$ $M(OH) = 17.008 \ Da$ $M(H) = 1.008 \ Da$ By convention, the weight percent is an average weight percentage based on the total weight of the cellulose repeat unit, including all substituents. The content of the methoxyl group is reported based on the mass of the methoxyl group (i.e., —OCH$_3$). The content of the hydroxyalkoxyl group is reported based on the mass of the hydroxyalkoxyl group (i.e., —O— alkylene-OH); such as hydroxypropoxyl (i.e., —O—CH$_2$CH(CH$_3$)—OH). The content of the aliphatic monovalent acyl groups is reported based on the mass of —C(O)—R$_1$ wherein R$_1$ is a monovalent aliphatic group, such as acetyl (—C(O)—CH$_3$). The content of the group of formula —C(O)—R—COOH is reported based on the mass of this group, such as the mass of succinoyl groups (i.e., —C(O)—CH$_2$—CH$_2$—COOH).

Another essential property of the esterified cellulose ether b) is its water-solubility. The esterified cellulose ether has a solubility in water of at least 2.0 weight percent at 2° C., i.e., it can be dissolved as an at least 2.0 weight percent solution, preferably at least 3.0 weight percent solution, more preferably at least 5.0 weight percent solution or even at least 10.0 weight solution in water at 2° C. Generally the esterified cellulose ether b) can be dissolved as up to 20 weight percent solution or in the most preferred embodiments even as up to 30 weight percent solution in water at a temperature of 2° C. The term "an x weight percent solution in water at 2° C." as used herein means that x g of the esterified cellulose ether b) is soluble in (100-x) g of water at 2° C.

In more general terms, the esterified cellulose ether b), in spite of its low degree of neutralization of the groups —C(O)—R—COOH, is soluble in an aqueous liquid at a temperature of less than 10° C., more preferably less than 8° C., even more preferably 5° C. or less, and most preferably up to 3° C., even when the esterified cellulose ether is blended with an aqueous liquid that does not increase the degree of neutralization of the esterified cellulose ether b) to more than 0.4 or a preferred range listed above, e.g., when the esterified cellulose ether is blended with only water, such as deionized or distilled water. Clear or turbid solutions with only a small portion of sediment or in the preferred embodiments even without sediment are obtained at 2° C. When the temperature of the prepared solution is increased to 20° C., no precipitation occurs.

The esterified cellulose ethers a) and b) comprised in the composition of the present invention generally have a viscosity of at least 1.2 mPa·s, preferably least 1.8 mPa·s, and more preferably least 2.4 mPa·s, and generally no more than 200 mPa·s, preferably no more than 100 mPa·s, more preferably no more than 50 mPa·s, and most preferably no more than 30 mPa·s, measured as a 2.0 weight percent solution of the esterified cellulose ether in 0.43 wt % aqueous NaOH at 20° C. according to "Hypromellose Acetate Succinate, United States Pharmacopia and National Formulary, NF 29, pp. 1548-1550".

The esterified cellulose ether b) generally has a weight average molecular weight $M_w$ of up to 500,000 Dalton, preferably up to 250,000 Dalton, more preferably up to 200,000 Dalton, most preferably up to 150,000 Dalton, and particularly up to 100,000 Dalton. Generally they have a weight average molecular weight $M_w$ of at least 10,000 Dalton, preferably at least 12,000 Dalton, more preferably at least 15,000 Dalton, and most preferably at least 20,000 Dalton, and particularly at least 30,000 Dalton. $M_w$ and the number average molecular weight $M_n$ are measured according to Journal of Pharmaceutical and Biomedical Analysis 56 (2011) 743 using a mixture of 40 parts by volume of acetonitrile and 60 parts by volume of aqueous buffer containing 50 mM $NaH_2PO_4$ and 0.1 M $NaNO_3$ as mobile phase. The mobile phase is adjusted to a pH of 8.0. The measurement of $M_w$ and $M_n$ is described in more details in the Examples.

The aqueous composition of the present invention generally comprises at least 5 percent, preferably at least 10 percent, more preferably at least 15 percent, most preferably at least 20 percent, and under some conditions even at least 25 percent of the esterified cellulose ether a) in dispersed state in the aqueous composition. The aqueous composition of the present invention generally comprises up to 40 percent or up to 35 percent of the esterified cellulose ether a) in dispersed state in the aqueous composition.

The aqueous composition of the present invention preferably comprises at least 1 percent, more preferably at least 2 percent, and most preferably at least 5 percent of the esterified cellulose ether b) in the aqueous composition. The aqueous composition of the present invention generally comprises up to 30 percent, preferably up to 15 percent, and more preferably up to 10 percent of the esterified cellulose ether b) in in the aqueous composition.

The weight ratio between the esterified cellulose ether a) and the esterified cellulose ether b) in the aqueous composition of the present invention preferably is at least 2:1, more preferably at least 5:1, and most preferably at least 10:1. The weight ratio between the esterified cellulose ether a) and the esterified cellulose ether b) in the aqueous composition preferably is up to 40:1, more preferably up to 30:1, and most preferably up to 20:1.

The aqueous composition of the present invention preferably comprises at least one surfactant. The total amount of the surfactant(s) generally is at least 0.05 percent, preferably at least 0.1 percent, more preferably at least 0.3 percent, even more preferably at least 0.5 percent, most preferably at least 0.8 percent, and particularly at least 1.0 percent, based on the total weight of the esterified cellulose ether(s). The total amount of the surfactants generally is up to 20 percent, preferably up to 15 percent, more preferably up to 12 percent, even more preferably up to 10 percent or 8 percent, and most preferably up to 6.0 percent, or even only up to 5.0 percent, based on the total weight of the esterified cellulose ethers a) and b). A surfactant is generally used to stabilize the dispersion, i.e., to keep the esterified cellulose ether particles a) dispersed in the aqueous phase.

A large variety of anionic, cationic and non-ionic surfactants exists. Well-known anionic surfactants are sodium alkyl sulfates, such as sodium dodecyl sulfate. Well-known non-ionic surfactants are ethylene oxide—propylene oxide block copolymers, such as Pluronic™ surfactants, or polyoxyethylene sorbitan monooleates, such as Polysorbate 80, also known under the trademark Tween 80.

A preferred surfactant is a salt of a fatty acid, preferably an ammonium, alkali metal or alkaline earth metal salt of a saturated or unsaturated fatty acid. Preferred fatty acid salts are ammonium, alkali metal or alkaline earth metal salts. A preferred ammonium ion is $NH_4^+$. Preferred alkali metal ions are the sodium or potassium ions. A preferred alkaline earth metal ion is the calcium ion. The fatty acids can be saturated or unsaturated. Exemplary of saturated fatty acids are caprylic acid, capric acid, lauric acid, myristic acid, palmitic acid, stearic acid, arachidic acid, behenic acid, lignoceric acid and cerotic acid. The unsaturated fatty acids can be mono-, di- or triunsaturated fatty acids, mono-unsaturated and di-unsaturated fatty acids being preferred. Exemplary of mono-unsaturated fatty acids are myristoleic acid, palmitoleic acid, sapienic acid, oleic acid, elaidic acid and vaccenic acid. Exemplary of di-unsaturated fatty acids are linoleic acid and linoelaidic acid. Ammonium, alkali metal and alkaline earth metal salts of stearic acid or oleic acid are most preferred, particularly those salts mentioned above. Aqueous dispersions comprising a salt of a fatty acid as a surfactant, their advantages and a process for preparing them are described in more detail in the co-pending International Patent Application PCT/US15/018390, filed 3 Mar. 2015, published as WO/2015/156922 and claiming priority of U.S. Provisional Application No. 61/976,726, filed 8 Apr. 2014, and in the co-pending International Patent Application PCT/US16/041455, filed on 8 Jul. 2016, claiming the priority of U.S. Provisional Application 62/197,605, filed 28 Jul. 2015.

The aqueous composition of the present invention is in the form of an aqueous dispersion, typically in the form of a stable dispersion. The median particle size, d50, of the dispersed esterified cellulose ether particles is preferably up to 7 micrometers, more preferably up to 4 micrometers, even more preferably up to 3 micrometers, and most preferably even only up to 2 micrometers. The median particle size, d50, of the dispersed esterified cellulose ether particles is typically 0.3 micrometers or more, more typically 0.5 micrometers or more, and most typically 0.7 micrometers or more. The particle size is measured by laser diffraction particle size analysis, e.g., using a Beckman Coulter laser diffraction particle size analyzer which is commercially available from Beckman Coulter, Calif. The median particle size d50 is the diameter where 50 volume percent of the particles have a smaller equivalent diameter and 50 volume percent have a larger equivalent diameter. Typically d90 is 0.7 micrometers or more, more typically 1.0 micrometers or more, and most typically 1.5 micrometers or more; and typically up to 12 micrometers, more typically up to 10 micrometers, even more typically up to 9 micrometers, most typically up to 7 micrometers and in many cases even only up to 5 micrometers, d90 being the diameter where 90 volume percent of the particles have a smaller equivalent diameter and the other 10 volume percent have a larger equivalent diameter. The equivalent particle diameter d is the diameter of a sphere having the same volume as the volume of a given particle. The mean particle diameter is typically 0.5 micrometers or more, more typically 0.7 micrometers or more, and most typically 0.8 micrometers or more; and typically up to 8 micrometers, more typically up to 6 micrometers, even more typically up to 4 micrometers, and most typically even only up to 3 micrometers.

The aqueous composition of the present invention comprises an aqueous diluent. The aqueous diluent is water, optionally mixed with a minor amount of an organic solvent. The aqueous diluent preferably consists of 50-100 weight percent, more preferably 65-100 weight percent, and most preferably 75-100 weight percent of water and preferably 0-50 weight percent, more preferably 0-35 weight percent, and most preferably 0-25 weight percent of an organic solvent, based on the total weight of water and the organic solvent. Useful organic solvents are polar organic solvents having one or more heteroatoms, such as oxygen, nitrogen or halogen like chlorine. More preferred organic solvents are alcohols, for example multifunctional alcohols, such as glycerol, or preferably monofunctional alcohols, such as methanol, ethanol, isopropanol or n-propanol; ethers, such as tetrahydrofuran, ketones, such as acetone; methyl ethyl ketone, or methyl isobutyl ketone; acetates, such as ethyl acetate; halogenated hydrocarbons, such as methylene chloride; or nitriles, such as acetonitrile. Preferably the aqueous composition of the present invention comprises water alone as aqueous diluent. The amount of the aqueous diluent is typically at least 50 percent, more typically at least 60 percent, and most typically at least 65 percent, based on the total weight of the aqueous composition. The amount of the aqueous diluent is typically no more than 85 percent, more typically no more than 80 percent, and most typically no more than 75 percent, based on the total weight of the aqueous composition.

In one embodiment the sum of the dispersed esterified cellulose ethers a) and b) described above, and optionally the salt(s) of a fatty acid c) amounts to at least 50 percent, typically at least 60 percent, and more typically at least 80 percent; and up to 100 percent, typically up to 95 percent, and more typically up to 90 percent of the total weight of the ingredients of the aqueous composition excluding the aqueous diluent. In another embodiment the sum of the esterified cellulose ethers a) and b) amounts to at least 50 percent, typically at least 60 percent, and more typically at least 80 percent; and up to 100 percent, typically up to 99 percent, more typically up to 95 percent, of the total polymer weight in the aqueous composition.

The aqueous composition of the present invention may further comprise optional ingredients, for example active ingredients, such as fertilizers, herbicides or pesticides, or biologically active ingredients, such as vitamins, herbals and mineral supplements and drugs; or adjuvants such as one or more plasticizers, coloring agents, pigments, opacifiers, flavor and taste improvers, antioxidants, and any combination thereof. Optional additives are preferably pharmaceutically acceptable. The amount of these optional ingredients is typically from 0 to 50 percent of the total weight of the ingredients of the aqueous composition excluding the aqueous diluent. Typically the amount is 1 percent or more, more typically 5 percent or more, and most typically 10 percent or more; and up to 40 percent, more typically up to 20 percent, and most typically up to 10 percent of the total weight of the ingredients of the aqueous composition excluding the aqueous diluent.

Useful plasticizers include phthalic esters, such as dimethyl-, diethyl-, and diisopropyl-phthalate; citric esters, such as triethyl-, tributyl-, acetyltriethyl- and acetyltributyl-citrate; phosphoric esters, such as triethyl-, tricresyl, and triphenyl-phosphate; alkyl lactate; glycol esters; glycerol and glycerol esters, such as glycerol triacetate also known as triacetine; sucrose esters; oils and fatty acid esters; butyl stearate; dibutyl sebacate; dibutyl tartrate; diisobutyl adipate, tributyrin; propylene glycol, castor oil, a phospholipid, lecithin; and combinations thereof. Useful plasticizers generally have a molecular weight of not more than 800 g/mol.

The aqueous composition may comprise a polymeric film forming aid in addition to the esterified cellulose ether b), for example gelatin, pullulan, non-enteric starch derivatives, such as hydroxypropyl starch; polyvinyl acetate (PVA); polyoxyethylene esters; polyethylene glycol and combinations thereof. However, if polymeric film forming aids are incorporated in the aqueous composition, their amount preferably is not more than 0.5%, more preferably not more than 0.2%, and even more preferably not more than 0.1%, based on the total weight of the aqueous composition of the present invention.

The aqueous composition of the present invention can be prepared by various methods. One method includes grinding the esterified cellulose ether a) in the presence of an aqueous diluent and optionally in the presence of one or more adjuvants. Another method includes melting the esterified cellulose ether at an elevated temperature, optionally in the presence of one or more adjuvants, and emulsifying the molten or softened mass in the aqueous diluent. The esterified cellulose ether b) can be subsequently blended with the dispersed particles of the esterified cellulose ether a). However, preparing an aqueous composition by simply physically blending an esterified cellulose ether a), an esterified cellulose ether b), a surfactant and an aqueous diluent at room temperature is usually not suitable for preparing a stable dispersion.

In one embodiment the aqueous composition of the present invention is produced in a process which comprises the step of grinding at least one esterified cellulose ether a) as described above in the presence of an above-described aqueous diluent. Any grinding device suitable for grinding esterified cellulose ethers in the presence of an aqueous diluent to a median particle size d50 as indicated further above can be used. Preferred grinding devices are wet grinding units such as media mills or bead mills. The grinding is typically conducted at a temperature of at least 2° C., more typically at least 15° C., and typically at a temperature of up to 40° C., more typically up to 35° C. Grinding is conducted for a sufficient time period to achieve an above-mentioned median particle size, d50, of the dispersed esterified cellulose ether particles.

In another embodiment the aqueous composition of the present invention is produced in a process which comprises the steps of melting at least one esterified cellulose ether a) as described above, emulsifying the molten esterified cellulose ether in an above-described aqueous diluent, and cooling the emulsion to form an aqueous dispersion. This embodiment of the process is preferably conducted in an extruder. Alternatively, a pressurized batch kneader can be used for conducting this embodiment of the process. The general process conditions and equipment which are useful to perform the process are disclosed in U.S. Pat. Nos. 5,539,021 and 7,763,676, the disclosure of which is incorporated herein by reference.

Preferably a surfactant, such as a salt of a fatty acid, and optionally one or more adjuvants are blended with the esterified cellulose ether before, during or after the step of grinding the esterified cellulose ether a) or before, during or after the step of emulsifying the molten esterified cellulose ether a) in the aqueous diluent. Preferably a surfactant of the type and amount described further above is added to the esterified cellulose ether a) before or during the above-mentioned grinding or emulsification of the esterified cellulose ether a) in the aqueous diluent.

The production of the dispersion of the esterified cellulose ether a), in the absence of the esterified cellulose ether b), is described in co-pending International Patent Application PCT/US15/018390, filed 3 Mar. 2015, published as WO/2015/156922 and claiming priority of U.S. Provisional Application No. 61/976,726, filed 8 Apr. 2014, and in the co-pending International Patent Application PCT/US16/041455, filed on 8 Jul. 2016, claiming the priority of U.S. Provisional Application 62/197,605, filed 28 Jul. 2015, all filed by the Applicants of the present patent application, and in the Examples of the present invention.

At least one esterified cellulose ether b) as described above is added before, during or after the step of grinding the esterified cellulose ether a) or before, during or after the step of emulsifying the molten esterified cellulose ether a) in the aqueous diluent. The esterified cellulose ether b) is advantageously added only after the grinding of the esterified cellulose ether a) or only after the steps of emulsifying the molten esterified cellulose ether a) in the aqueous diluent and after cooling the emulsion. I.e., the esterified cellulose ether b) is preferably added only after the preparation of the aqueous dispersion comprising the dispersed particles of the esterified cellulose ether a). The esterified cellulose ether b) is preferably added to the aqueous dispersion comprising the dispersed particles of the esterified cellulose ether a) at a temperature of from 1 to 25° C., more preferably from 4 to 15° C.

The production of the esterified cellulose ether b) is described in copending International Patent Application No. PCT/US16/021330, filed on 8 Mar. 2016, which claims the priority of U.S. Provisional Application No. 62/133,514, filed 16 Mar. 2015, and International Patent Application No. PCT/US16/021326, filed on 8 Mar. 2016, which claims the priority of U.S. Provisional Application No. 62/133,518, filed on 16 Mar. 2015, all filed by the Applicants of the present patent application, and in the Examples of the present invention. These International Patent Applications describe the reaction of a cellulose ether with an aliphatic monocarboxylic acid anhydride, such as acetic anhydride, butyric anhydride or propionic anhydride, and with a dicarboxylic acid anhydride, such as succinic anhydride, in an aliphatic carboxylic acid, such as acetic acid, as a reaction diluent.

In the International Patent Application No. PCT/US16/021330, filed on 8 Mar. 2016, which claims the priority of U.S. Provisional Application No. 62/133,514, the esterified cellulose ether b) is produced in the absence of an esterification catalyst, and in particular in the absence of an alkali metal carboxylate. This is in contrast to known processes. According to the general procedure described in the International Patent Application No. PCT/US16/021330, a cellulose ether, preferably one of the type listed further above, is reacted with an aliphatic monocarboxylic acid anhydride, such as acetic anhydride, butyric anhydride and propionic anhydride, and with a dicarboxylic acid anhydride, such as succinic anhydride. The molar ratio between the anhydride of an aliphatic monocarboxylic acid and the anhydroglucose units of the cellulose ether generally is from 0.1/1 to 7/1, preferably from 0.3/1 to 3.5/1, and more preferably from 0.5/1 to 2.5/1. The molar ratio between the anhydride of a dicarboxylic acid and the anhydroglucose units of cellulose ether preferably is from 0.1/1 to 2.2/1, preferably from 0.2/1 to 1.2/1, and more preferably from 0.3/1 to 0.8. The molar number of anhydroglucose units of the cellulose ether can be determined from the weight of the cellulose ether used as a starting material, by calculating the average molecular weight of the substituted anhydroglucose units from the DS(alkoxyl) and MS(hydroxyalkoxyl). The esterification of the cellulose ether is conducted in an aliphatic carboxylic acid as a reaction diluent, such as acetic acid, propionic acid, or butyric acid, most preferably acetic acid. The molar ratio [aliphatic carboxylic acid/anhydroglucose units of cellulose ether] generally is at least 0.7/1, preferably at least 1.2/1, and more preferably at least 1.5/1. The molar ratio [aliphatic carboxylic acid/anhydroglucose units of cellulose ether] is generally up to 10/1, and preferably up to 9/1. Lower ratios, such as up to 7/1 or even only up to 4/1 and under optimized conditions even only up to 2/1 can also be used, which makes optimal use of the amount of reaction diluent needed. In contrast to the known processes, the esterified cellulose ethers of the present invention are produced in the absence of an esterification catalyst, and in particular in the absence of a alkali metal carboxylate. The reaction temperature for the esterification is generally from 60° C. to 110° C., preferably from 70° C. to 100° C. The esterification reaction is typically completed within 2 to 8 hours, more typically within 3 to 6 hours. After completion of the esterification reaction, the esterified cellulose ether can be precipitated from the reaction mixture in a known manner, for example as described in U.S. Pat. No. 4,226,981, International Patent Application WO 2005/115330, European Patent Application EP 0 219 426 or International Patent Application WO2013/148154. The precipitated esterified cellulose ether is subsequently washed with water, preferably at a temperature of from 70 to 100° C.

In another aspect of the invention the aqueous composition of the present invention may be used for coating dosage forms, such as tablets, granules, pellets, caplets, lozenges, suppositories, pessaries or implantable dosage forms, to form a coated composition. The coating can be carried out in a known manner, for example by known dipping or spraying processes.

In yet another aspect of the invention the aqueous composition of the present invention may be used for the manufacture of capsules shells in a process which comprises the step of contacting the aqueous composition with dipping pins. The general process conditions and equipment which may be used to prepare capsules shells are described in International Patent Application Nos. WO 2013/164122 and WO 2013/164121, the disclosures of which are incorporated herein by reference.

The aqueous composition of the present invention is particularly useful for coating dosage forms or for the formation of capsules shells, all preferably for enteric use, i.e., coatings or capsules shells that are dissolved in the intestinal canals to release the active ingredient like a drug contained in the dosage form or in the capsules.

Some embodiments of the invention will now be described in detail in the following Examples.

EXAMPLES

Unless otherwise mentioned, all parts and percentages are by weight. In the Examples the following test procedures are used.

Viscosity of Hydroxypropyl Methyl Cellulose Acetate Succinate (HPMCAS)

A 2.0% by weight solution of the HPMCAS in 0.43 wt. % aqueous NaOH is prepared as described in "Hypromellose Acetate Succinate, United States Pharmacopia and National Formulary, NF 29, pp. 1548-1550, followed by an Ubbelohde viscosity measurement at 20° C. according to DIN 51562-1:1999-01 (January 1999).

Content of Ether and Ester Groups of HPMCAS

The content of ether groups in HPMCAS is determined in the same manner as described for "Hypromellose", United States Pharmacopeia and National Formulary, USP 35, pp 3467-3469. The ester substitution with acetyl groups (—CO—CH$_3$) and the ester substitution with succinoyl groups (—CO—CH$_2$—CH$_2$—COOH) are determined according to Hypromellose Acetate Succinate, United States Pharmacopia and National Formulary, NF 29, pp. 1548-1550". Reported values for ester substitution are corrected for volatiles (determined as described in section "loss on drying" in the above HPMCAS monograph).

Apparent Viscosity of the Aqueous Composition Comprising HPMCAS as a Function of Temperature The apparent viscosity of the aqueous dispersion comprising HPMCAS is measured as a function of temperature according to a temperature sweep experiment performed with a Anton Paar MCR 501 rheometer with a CC-27 cup geometry and a 4-blade vane geometry ST26-4V-20 over a temperature range of 10 to 50° C. with a heating rate of 0.5° C./min and a constant speed of the vane geometry of 40 rpm and a measurement point duration of 0.25 min. Prior to this temperature sweep testing the material is treated for 30 min at 10° C. at 250 rpm (high shear). A sample volume of 20 ml is used for these measurements. The sample has been stored at room temperature prior to the viscosity measurement.

Determination of Viscosity of the Aqueous Composition depending on Shear Rate

The viscosity of the aqueous HPMCAS dispersion comprising HPMCAS is measured at 21° C. with a Haake RS600 rheometer (from Thermo Fischer Scientific, Karlsruhe) with a cone & plate geometry (C-60/1°) in a steady shear flow curve experiment over a steady shear rate range from 0.1-1000 s$^{-1}$ with 5 data points each decade.

Properties of the Dispersion Comprising Dispersed HPMCAS Particles a)

HPMCAS Particle Size Measurement in the HPMCAS Dispersion

To measure particle sizes 1-2 g of the aqueous HPMCAS dispersion that has been produced as described below is diluted in 20 ml of purified water. The particle size in the diluted dispersion is measured by laser diffraction particle size analysis using a Beckman Coulter LS 13 320 laser diffraction particle size analyzer which is commercially available from Beckman Coulter, Calif. The Universal Liquid Module (ULM) with a Fraunhofer optical model, a Polarization Intensity Differential Scattering (PIDS) system and a sonication control unit are used. In the sonication control unit the HPMCAS dispersion is subjected to ultrasonic treatment for a time period of up to 120 seconds during the HPMCAS addition (about 30 seconds) and particle size measurement (about 90 seconds).

Determination of Solids Content in the HPMCAS Dispersion

The solids content is determined using a moisture balance (Mettler Toledo Advanced Moisture Analyzer, Model HB43-S). Instrument settings are as follows: 3 g dispersion using the Rapid drying program with a temperature set point of 120° C. (40% overshoot for first 3 minutes) with switch-off criteria 5 (less than 1 mg weight change over 140 seconds). Upon drying to remove water, the residual solids content (including all additives) is weighed.

Properties of the Water-Soluble HPMCAS b)

Determination of $M_w$ and $M_n$ $M_w$ and $M_n$ are measured according to Journal of Pharmaceutical and Biomedical Analysis 56 (2011) 743 unless stated otherwise. The mobile phase is a mixture of 40 parts by volume of acetonitrile and 60 parts by volume of aqueous buffer containing 50 mM NaH$_2$PO$_4$ and 0.1 M NaNO$_3$. The mobile phase is adjusted to a pH of 8.0. Solutions of the cellulose ether esters are filtered into a HPLC vial through a syringe filter of 0.45 µm pore size. The exact details of measuring $M_w$ and $M_n$ are disclosed in the International Patent Application No. WO 2014/137777 in the section "Examples" under the title "Determination of $M_w$, $M_n$ and $M_z$".

Water-Solubility of the Water-Soluble HPMCAS b)

A 2 wt. percent mixture of HPMCAS and water is prepared by mixing 2.0 g HPMCAS, based on its dry weight, with 98.0 g water under vigorous stirring at 0.5° C. for 16 hours. The temperature of the mixture of HPMCAS and water is then increased to 2° C. The water solubility of the esterified cellulose ether is determined by visual inspection. The determination whether the HPMCAS is water-soluble at 2% at 2° C. or not is done as follows. "Water soluble at 2%—yes" means that a solution without sediment is obtained according to the procedure above. "Water soluble at 2%—no" means that at least a significant portion of the HPMCAS remains undissolved and forms sediment when mixing 2.0 g HPMCAS, based on its dry weight, with 98.0 g water according to the procedure above. "Water soluble at 2%—partially" means that only a small portion of the HPMCAS remains undissolved and forms sediment when mixing 2.0 g HPMCAS, based on its dry weight, with 98.0 g water according to the procedure above.

Production of the Dispersion Comprising Dispersed HPMCAS Particles a)

To produce an aqueous HPMCAS dispersion, HPMCAS is used that has 23.0% methoxyl groups ($DS_{methoxyl}$=1.89), 7.3% hydroxypropoxyl groups ($MS_{hydroxypropoxyl}$=0.25), 9.1% acetyl groups ($DS_{acetyl}$=0.54), 11.6% succinoyl groups ($DS_{succinoyl}$=0.29), and a viscosity of 2.9 mPa·s, measured as a 2.0% by weight solution of the HPMCAS in 0.43 wt % aqueous NaOH.

HPMCAS and sodium stearate as surfactant are added to water recirculating through a Drais DCP-12 Advantis media mill (1.0 mm ceramic media, 0.5 mm screen size). The mill speed is initially set at 1400-1500 rpm and then reduced as necessary down to about 1100-1400 rpm to control the mill outlet temperature.

HPMCAS and sodium stearate are pre-blended at a weight ratio to provide a percentage of 4.8% sodium stearate based on HPMCAS. The pre-blend of HPMCAS and sodium stearate is loaded in portions to water recirculating through the mill. Addition continues until a total solids loading of about 30% is achieved, based on the total weight of the composition. The percentage of HPMCAS, based on the total weight of the composition, is calculated from the measured solids content and the given weight ratio between HPMCAS and the sodium stearate. Following the addition of all solids, milling continues for about 3 hours until the final particle size is obtained. During the milling process, mild heat treatment is applied by adjusting the mill speed and the setpoint for the chiller system used to provide cooling to the mill jacket, tank and heat exchangers. The maximum temperature during milling is 39-41° C. The produced aqueous dispersion has a HPMCAS content of 28.5 percent, based on the total weight of the HPMCAS dispersion.

The particle size distribution of the freshly produced aqueous HPMCAS dispersion is determined by laser diffraction particle size analysis as described further above. The mean particle diameter is 1.7 μm, the median particle size, d50, is 1.2 μm, and the particle size d90 is 3.7 μm. The median particle size, d50, is the size at which 50 volume percent of the particles have a smaller equivalent diameter and 50 volume percent have a larger equivalent diameter; d90 is the diameter where 90 volume percent of the particles have a smaller equivalent diameter and the other 10 volume percent have a larger equivalent diameter.

Production of the Water-Soluble HPMCAS b)

The water-soluble HPMCAS polymer is produced as described in co-pending

International Patent Application No. PCT/US16/021330, filed on 8 Mar. 2016, which claims the priority of U.S. Provisional Application No. 62/133,514, filed 16 Mar. 2015.

Succinic anhydride and acetic anhydride are dissolved at 70° C. in glacial acetic acid. Then hydroxypropyl methyl cellulose (HPMC, water free) is added under stirring. The amounts are listed in Table 1 below. The amount of HPMC is calculated on a dried basis. No amount of sodium acetate is added.

The HPMC has a methoxyl substitution ($DS_M$) and hydroxypropoxyl substitution ($MS_{HP}$) as listed in Table 2 below and a viscosity of 3.0 mPa·s, measured as a 2% solution in water at 20° C. according to ASTM D2363-79 (Reapproved 2006). The weight average molecular weight of the HPMC is about 20,000 Dalton. The HPMC is commercially available from The Dow Chemical Company as Methocel E3 LV Premium cellulose ether. Then the reaction mixture is heated up to 85-110° C. for 2 hours. Then the crude product is precipitated by adding 1-2 L of water having a temperature of 21° C.

Subsequently the precipitated product is separated from the mixture by filtration. The precipitated reaction mass is split in two halves. The first half is washed several times with water having a temperature of 95° C. (Sample 1). The second half is washed several times with water having a temperature of 21° C. (Sample 2). Then the products are isolated by filtration and dried at 55° C. overnight.

The properties of the water-soluble HPMCAS samples are listed in Table 2 below. In Table 2 the abbreviations have the following meanings:

$DS_M$=DS(methoxyl): degree of substitution with methoxyl groups;

$MS_{HP}$=MS(hydroxypropoxyl): molar subst. with hydroxypropoxyl groups;

$DS_{Ac}$: degree of substitution of acetyl groups;

$DS_s$: degree of substitution of succinoyl groups.

TABLE 2

| water-soluble HPMCAS sample | Molecular weight (kDA) | | 2% viscosity in NaOH [mPa·s] | Methoxyl (%) | Hydroxypropoxyl (%) | Acetyl (%) | Succinoyl (%) | $DS_M$ | $MS_{HP}$ | $DS_{Ac}$ | $DS_s$ | Sum $DS_{Ac}+DS_s$ | Water-soluble at 2% |
|---|---|---|---|---|---|---|---|---|---|---|---|---|---|
| | $M_n$ | $M_w$ | | | | | | | | | | | |
| 1 | 20 | 35 | 3.1 | 26.1 | 8.0 | 6.2 | 6.1 | 1.95 | 0.25 | 0.33 | 0.14 | 0.47 | Yes |
| 2 | 32 | 54 | 3.9 | 24.9 | 7.8 | 6.5 | 6.5 | 1.86 | 0.24 | 0.35 | 0.15 | 0.5 | Yes |

TABLE 1

| water-soluble HPMCAS sample | HPMC* | | Glacial acetic acid | | Succinic anhydride | | Acetic anhydride | | Sodium acetate | | Temperature of washing water, °C. |
|---|---|---|---|---|---|---|---|---|---|---|---|
| | g | Mol | g | mol/mol HPMC | g | mol/mol HPMC | g | mol/mol HPMC | g | mol/mol HPMC | |
| 1 | 350 | 1.72 | 179.5 | 1.7 | 179.5 | 1.04 | 538.5 | 3.18 | 0 | 0 | 95 |
| 2 | 350 | 1.72 | 179.5 | 1.7 | 179.5 | 1.04 | 538.5 | 3.18 | 0 | 0 | 21 |

Comparative Example A

The dispersion comprising dispersed HPMCAS particles a), which has been produced as described further above, is not mixed with any other component and is used for analysis as such. The total solids content in the dispersion is 29.9 percent; thereof the HPMCAS content is 28.5 percent and the sodium stearate content is 1.4 percent, each based on the total weight of the dispersion.

Example 1

10 parts of Sample 2 of the water-soluble HPMCAS are dissolved in 90 parts of water having a temperature of 4° C., which results in a 10 wt.-% aqueous solution of HPMCAS. Alternatively, 10 parts of Sample 2 of the water-soluble HPMCAS can be dissolved in 90 parts of water having a temperature of 2° C. Sample 2 of the water-soluble HPMCAS has a solubility in water of at least 10 weight percent at 2° C.

100 g of the dispersion of Comparative Example A is mixed with 17 g of the 10 wt.-% aqueous solution of HPMCAS at a temperature of 10° C., i.e., the weight ratio between dispersed HPMCAS particles a) and the water-soluble HPMCAS b) is about 17:1.

Figure 1:
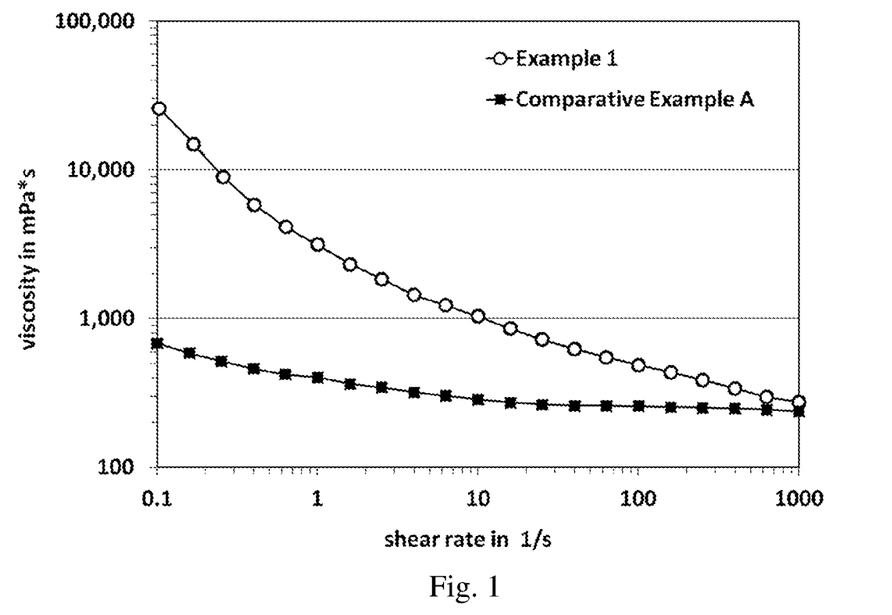
FIG. 1 illustrates the viscosities at 21° C. of an aqueous composition of the present invention and of a comparative aqueous composition as a function of the shear rate at which the compositions are sheared.

The viscosities of the dispersion of Comparative Example A and of the aqueous composition of Example 1 at 21° C. as a function of shear rate are measured with a Haake RS600 rheometer as described in more details above. The results are shown in FIG. 1.

Figure 2:
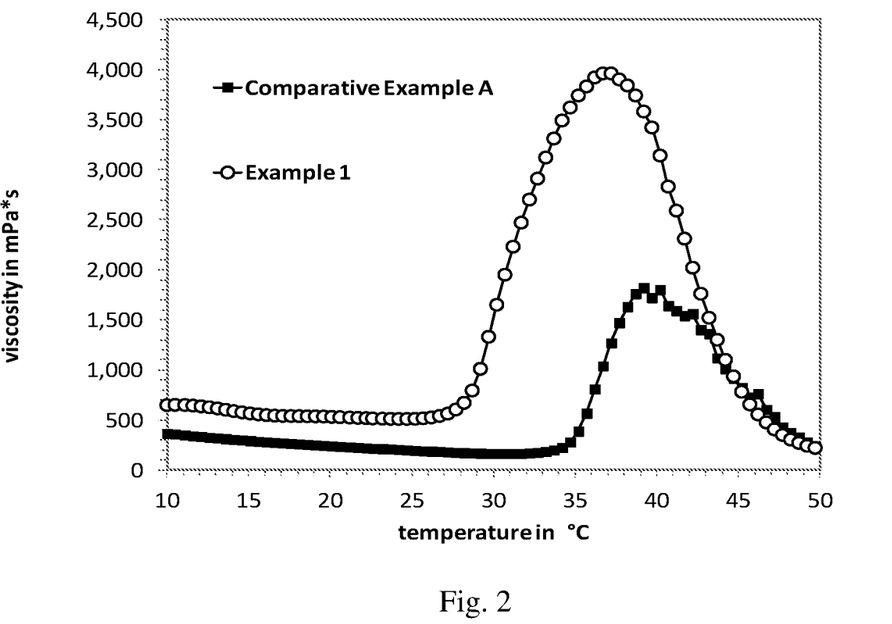
FIG. 2 illustrates the viscosities of the same aqueous composition of the present invention and of the same comparative aqueous composition as a function of their temperatures.

The apparent viscosities of the aqueous compositions of Example 1 and of Comparative Example A as a function of their temperatures are also measured as described further above. Prior to this temperature sweep testing the material is treated for 30 min at 10° C. at 250 rpm, as described further above. The results are shown in FIG. 2.

Examples 2 and 3

10 parts of Sample 1 of the water-soluble HPMCAS are dissolved in 90 parts of water having a temperature of 4° C., which results in a 10 wt.-% aqueous solution of HPMCAS. Alternatively, 10 parts of Sample 1 of the water-soluble HPMCAS can be dissolved in 90 parts of water having a temperature of 2° C. Sample 1 of the water-soluble HPMCAS has a solubility in water of at least 10 weight percent at 2° C.

In Example 2 21.0 g of this 10 wt.-% aqueous solution of HPMCAS is mixed with 70 g of the dispersion of Comparative Example A at a temperature of 10° C.

In Example 3 31.5 g of this 10 wt.-% aqueous solution of HPMCAS is mixed with 70 g of the dispersion of Comparative Example A at a temperature of 10° C.

The viscosities of the dispersion of Comparative Example A and of the aqueous compositions of Example 1 and 2 at 21° C. as a function of shear rate are measured with a Haake RS600 rheometer as described in more details above. The results are shown in FIG. 3.

The apparent viscosities of the aqueous compositions of Examples 2 and 3 and of Comparative Example A as a function of their temperatures are also measured as described further above. Prior to this temperature sweep testing the material is treated for 30 min at 10° C. at 250 rpm, as described further above. The results are shown in FIG. 4.

Figure 3:
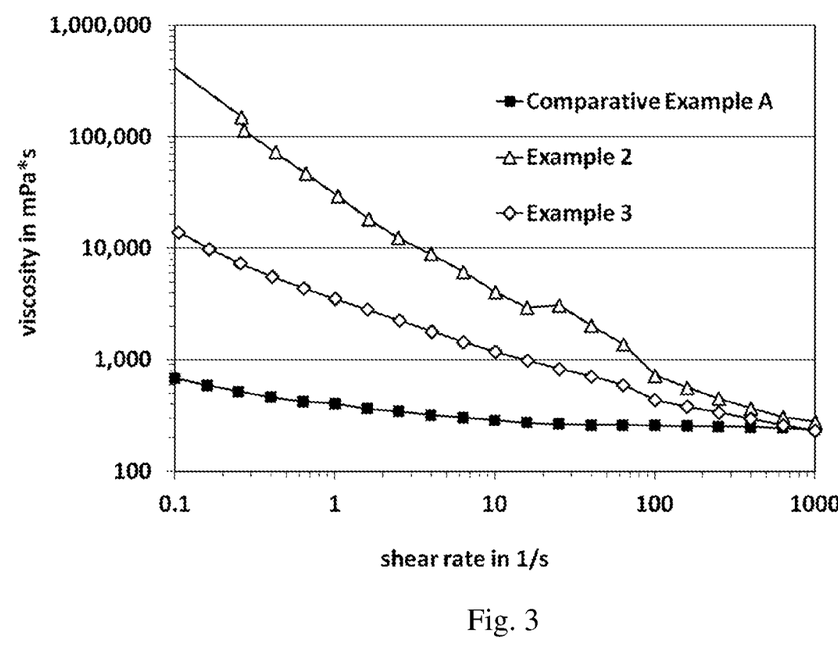
FIG. 3 illustrates the viscosities at 21° C. of two other aqueous compositions of the present invention and of a comparative aqueous composition as a function of the shear rate at which the compositions are sheared.

FIGS. 1 and 3 illustrate that the viscosities of the aqueous compositions of Example 1, 2 and 3 at low shear rate at 21° C. are much higher than that of Comparative Example A. The surprisingly high viscosity of the aqueous compositions of Example 1, 2 and 3 at a low shear rate is desirable at some occurrences where the aqueous dispersion is subjected to low shear, e.g. when the aqueous dispersion is gently agitated for producing coatings or for forming capsule shells on dipping pins. The viscosity increase at constant temperature, e.g. at 21° C., is of great advantage as it increases the adherence of the composition to the surface of the substrate to be coated, such as tablets, or to dipping pins in the case of capsule production.

On the other hand, if a low viscosity and a good processability of the aqueous composition at 21° C. is desired for other end-uses, such as spray-coating, this can be achieved by high shearing. At increased shear, e.g. at 200 sec$^{-1}$ or more or even at 1000 sec$^{-1}$ or more, the viscosity of the aqueous compositions of Example 1, 2 and 3 is reasonably low and very similar or even essentially identical to the viscosity of the aqueous composition of Comparative Example A.

Figure 4:
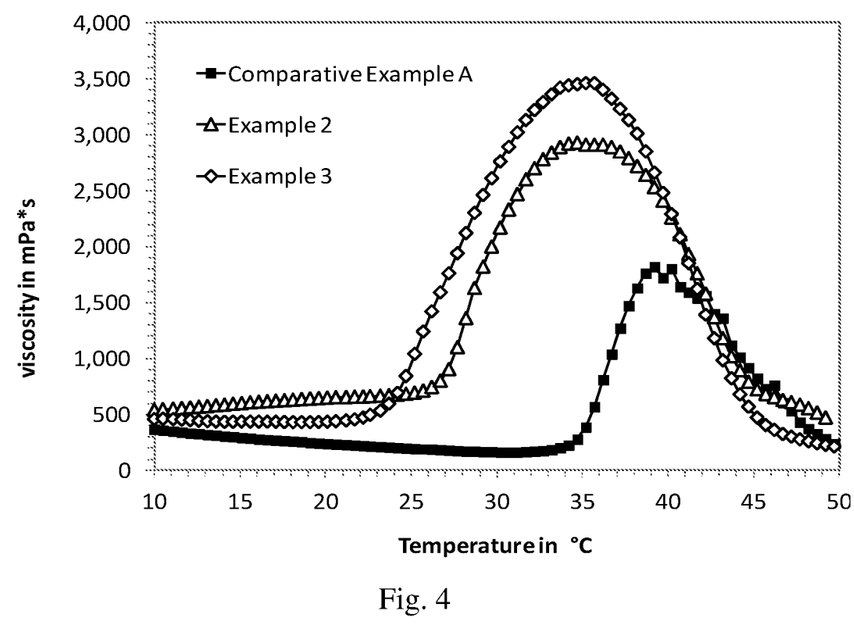
FIG. 4 illustrates the viscosities of these two aqueous compositions of the present invention and of the comparative aqueous composition as a function of their temperatures.

FIGS. 2 and 4 illustrate that due to the addition of the water-soluble HPMCAS the phase transition temperature of the aqueous composition and the viscosity can be adjusted to the needs in specific end-uses. When heating the aqueous compositions of Examples 1, 2 and 3 above the phase transition temperature a considerably higher viscosity is achieved than in Comparative Example A. Also, the phase transition temperatures can be adjusted and controlled to a large extent due to the addition of the water-soluble HPMCAS. On the other hand, the viscosities of the aqueous compositions of Example 1, 2 and 3 at room temperature are not much higher than that of Comparative Example A. This facilitated the handling of the compositions at room temperature.

Comparative Example B

To test the usefulness of the compositions of the aqueous composition of the present invention for the formation of capsules, the viscosity of the composition upon addition of triethyl citrate (TEC) is evaluated. TEC is a well-known film-forming aid used in capsule production.

In Comparative Example B triethyl citrate (TEC) is added drop wise to the dispersion of Comparative Example A. The amount of TEC is 20 percent, based on the weight of HPMCAS.

Examples 4 and 5

10 parts of Sample 2 of the water-soluble HPMCAS are dissolved in 90 parts of water having a temperature of 4° C., which results in a 10 wt.-% aqueous solution of HPMCAS.

In Example 4 19.95 g of the 10 wt.-% aqueous solution of HPMCAS is mixed with 70 g of the dispersion of Comparative Example A at a temperature of 10° C. TEC is added drop wise to the resulting aqueous composition. The TEC amount is 20%, based on the total weight of HPMCAS in the aqueous composition. Additionally 18.9 g of distilled water is added.

In Example 5 39.9 g of the 10 wt.-% aqueous solution of HPMCAS is mixed with 70 g of the dispersion of Comparative Example A at a temperature of 10° C. TEC is added drop wise to the resulting aqueous composition. The TEC amount is 20%, based on the total weight of HPMCAS in the aqueous composition. Additionally 9.45 g of distilled water is added.

The apparent viscosities of the aqueous compositions of Comparative Example B and of Examples 4 and 5 as a function of their temperatures are measured as described further above. The results are shown in FIG. 5.

Figure 5:
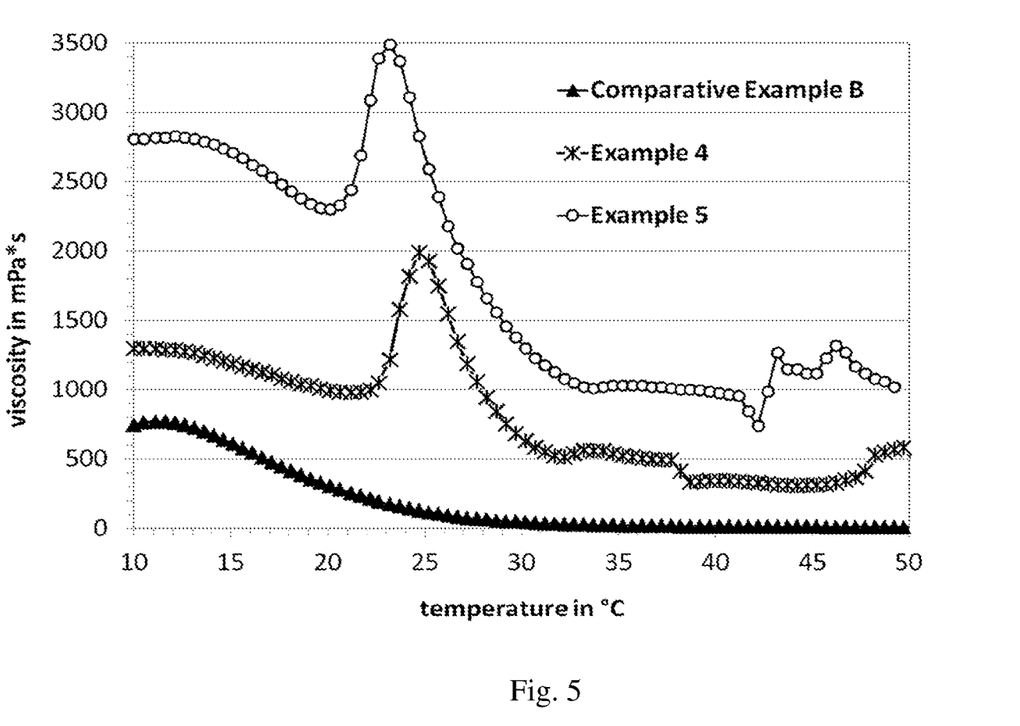
FIG. 5 illustrates the viscosities of yet two other aqueous compositions of the present invention and of a comparative aqueous composition, each comprising a plasticizer, as a function of their temperatures.

FIG. 5 illustrates that the viscosities of the aqueous compositions of Examples 4 and 5 start to increase significantly at a temperature of about 23° C. or 21° C., respectively, designated as "phase transition temperature". This viscosity increase is important as it improves adherence of the aqueous composition to dipping pins.

Preparation of Capsule Bodies

Molding pins are pre-heated to a temperature of 70° C. and then dipped into the HPMCAS composition of Example 5 having a temperature of 10° C. The pins are then withdrawn from the HPMCAS dispersion and a film is formed on the molding pins. The films on the molding pins are dried in a drying chamber having a temperature of 80° C. for 120 min. Capsule bodies result after drying.

The invention claimed is:

1. An aqueous composition comprising
    a) dispersed particles of a hydroxypropyl methylcellulose acetate succinate wherein the total degree of ester substitution is at least 0.75 and the degree of neutralization of the succinoyl groups is not more than 0.4, and
    b) a hydroxypropyl methylcellulose acetate succinate wherein I) the degree of neutralization of the succinoyl groups is not more than 0.4, II) the total degree of ester substitution is from 0.03 to 0.67, and III) the hydroxypropyl methylcellulose acetate succinate b) has a solubility in water of at least 2.0 weight percent at 2° C.

2. The aqueous composition of claim 1 comprising at least 15 percent of the dispersed particles a), based on the total weight of the aqueous composition.

3. The aqueous composition of claim 1 comprising at least 2 percent of the hydroxypropyl methylcellulose acetate succinate b), based on the total weight of the aqueous composition.

4. The aqueous composition of claim 1, wherein the median particle size, d50, of the dispersed hydroxypropyl methylcellulose acetate succinate particles a) is up to 7 micrometers, such median particle size (d50) being the size at which 50 volume percent of the particles have a smaller equivalent diameter and 50 volume percent have a larger equivalent diameter.

5. The aqueous composition of claim 1, wherein the total degree of ester substitution of the dispersed hydroxypropyl methylcellulose acetate succinate particles a) is from 0.75 to 1.10.

6. The aqueous composition of claim 1, wherein the total degree of ester substitution of the hydroxypropyl methylcellulose acetate succinate b) is from 0.20 to 0.60.

7. The aqueous composition of claim 1 wherein the aqueous composition additionally comprises c) 0.05 to 20 percent of a salt of a fatty acid, based on the total weight of the hydroxypropyl methylcellulose acetate succinate a) and b).

8. The aqueous composition of claim 1 wherein the hydroxypropyl methylcellulose acetate succinate a) and b) amount to at least 50 percent of the total polymer weight in the aqueous composition.

9. The aqueous composition of claim 1 wherein the hydroxypropyl methylcellulose acetate succinate a) and b) amount to at least 80 percent of the total polymer weight in the aqueous composition.

10. A dosage form being coated with a coating prepared from the aqueous composition of claim 1.

11. A capsule shell made from the aqueous composition of claim 1.

12. A capsule comprising a capsule shell of claim 11 and further comprising a drug or a nutritional or food supplement or a combination thereof.

13. A process for producing capsule shells comprising the steps of providing the aqueous composition of claim 1,
    pre-heating molding pins to a temperature higher than the aqueous composition,
    dipping the pre-heated molding pins into the aqueous composition,
    forming a film on said molding pins by withdrawing said pins from said aqueous composition, and
    drying the film on the molding pins.

14. The aqueous composition of claim 5, wherein the total degree of ester substitution of the hydroxypropyl methylcellulose acetate succinate b) is from 0.20 to 0.60.

15. The aqueous composition of claim 1, wherein the degree of neutralization of the succinoyl groups in both a) and b) are not more than 0.2.

16. The aqueous composition of claim 1, wherein the degree of neutralization of the succinoyl groups in both a) and b) are not more than 0.1.

17. The aqueous composition of claim 1, wherein the total degree of ester substitution of the hydroxypropyl methylcellulose acetate succinate b) is from 0.10 to 0.65.

18. The aqueous composition of claim 1, wherein the hydroxypropyl methylcellulose acetate succinate b) has a degree of substitution of acetyl groups of from 0.20 to 0.60 or a degree of substitution of succinoyl groups of from 0.05 to 0.45.

19. The aqueous composition of claim 1, wherein the hydroxypropyl methylcellulose acetate succinate b) has a solubility in water of at least 5.0 weight percent at 2° C.

20. The aqueous composition of claim 1, wherein the hydroxypropyl methylcellulose acetate succinate b) has a solubility in water of at least 10.0 weight percent at 2° C.

21. The aqueous composition of claim 1, wherein the total degree of ester substitution of the hydroxypropyl methylcellulose acetate succinate b) is from 0.20 to 0.50.

* * * * *